United States Patent [19]
McKinney

[11] 4,299,572
[45] Nov. 10, 1981

[54] DENTAL SAW BLADE

[76] Inventor: David D. McKinney, 110 Spring Forest Rd., Greenville, S.C. 29615

[21] Appl. No.: 90,093

[22] Filed: Nov. 1, 1979

[51] Int. Cl.³ .............................................. A61C 3/02
[52] U.S. Cl. ................................................... 433/144
[58] Field of Search .......................... 30/14.5, 31 AD; 145/31 R, 31 A; 433/144; 83/848, 835

[56] References Cited
U.S. PATENT DOCUMENTS 1,381,478  6/1921  Lawrence .............................. 83/851
2,741,279  4/1956  Stratton ................................. 83/850

Primary Examiner—Robert Peshock
Attorney, Agent, or Firm—Bailey, Dority & Flint

[57] ABSTRACT

A saw blade is disclosed for sawing a working model of a dental arch used in fixed crown and bridge work wherein the blade includes a first number of linear aligned saw teeth and a second number of laterally offset saw teeth which may be pulled or pushed into a cut initiated in the dental stone by the straight teeth for faster and straighter sawing.

3 Claims, 4 Drawing Figures

DENTAL SAW BLADE

BACKGROUND OF THE INVENTION

In dental work involving fixed crown and bridge work, a plaster or stone working model of the patient's dental arch is made and the teeth to which the crown or bridge work is to be fitted are then sectioned and sawed from the dental arch for easier working. Heretofore, ordinary dental saw blades have been utilized which are similar to a jigsaw blade. Due to the nature of the plaster or stone material, the life of a conventional blade is fairly short and as the blade becomes dull, it becomes more difficult to make a straight cut in the stone arch of the working model which is necessary to the accurate sectioning of the teeth to which the bridge or crown is to be fixed.

SUMMARY OF THE INVENTION

It has been found that a dental saw blade can be had for sawing dental stone by providing a saw blade having a first section of linearly aligned saw teeth and a second section of saw teeth blending into the first section which includes a number of laterally offset saw teeth. It has been found that a cut started by the first section of saw teeth may be finished by the second section of saw teeth and that a faster and straighter cut is provided in a manner which prolongs the life of the saw blade.

Accordingly, an important object of the present invention is the provision of a saw blade for sawing dental stone in working models of dental arches which cuts faster and affords a more accurate sectioning of the dental arch.

Another important object of the present invention is to provide a dental saw blade for sawing dental stone in which the life of the saw blade is prolonged.

BRIEF DESCRIPTION OF THE DRAWING

The construction designed to carry out the invention will be hereinafter described, together with other features thereof.

The invention will be more readily understood from a reading of the following specification and by reference to the accompanying drawing forming a part thereof, wherein an example of the invention is shown and wherein.

DESCRIPTION OF A PREFERRED EMBODIMENT

The invention relates to a saw blade for sawing a working model of a dental arch formed from dental plaster or stone wherein the blade includes a longitudinal shank portion A extending the length of the blade. A first section B of saw teeth is carried by the shank portion having a number of saw teeth 10 in generally linear alignment one behind the other. A second section C of saw teeth 12 and 14 is carried by the shank portion in a laterally offset manner with adjacent saw teeth being offset with respect to one another in lateral direction relative to the linear alignment of the first section of saw teeth. The first and second sections of saw teeth join with one another enabling the second section of teeth to enter the cut initiated by the first section of teeth to provide a faster and straighter cutting of the stone work. For this purpose, intermediate teeth 16 may be provided to blend the straight and offset teeth section into one another which are offset gradually.

Figure 1:
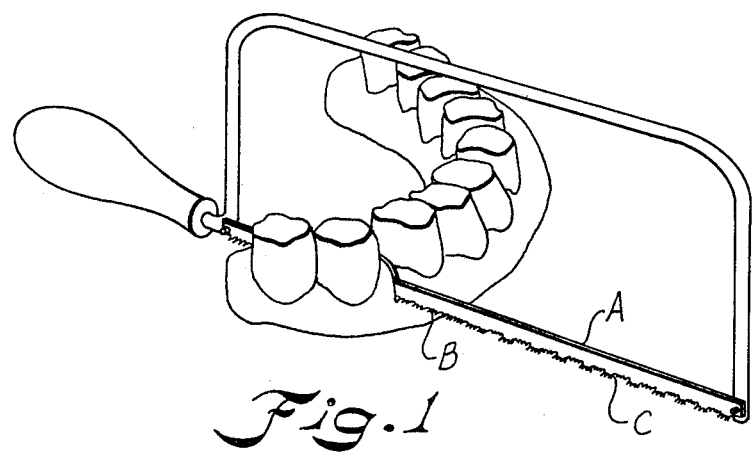
FIG. 1 is a perspective view illustrating a dental arch model and dental saw blade according to the invention.
Figure 2:
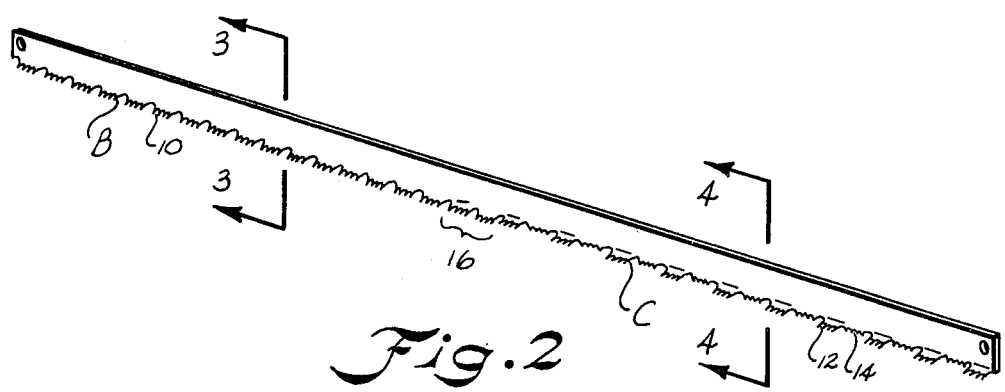
FIG. 2 is a perspective view illustrating a dental saw blade constructed according to the invention.
Figure 3:
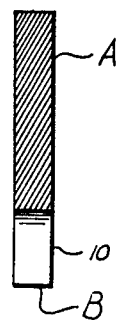
FIG. 3 is a sectional view along line 3—3 of FIG. 2.

FIG. 3 illustrates the first section of saw teeth B wherein the individual saw teeth 10 are aligned one behind the other in a straight row.

Figure 4:
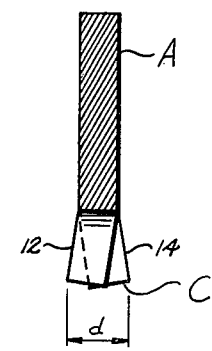
FIG. 4 is a section view taken along line 4—4 of FIG. 2.

FIG. 4 illustrates the second section C wherein the individual saw teeth 12 and 14 which are adjacent with one another are offset laterally relative to each other. In the one embodiment a lateral separation d between offset teeth 12 and 14 has been utilized equal approximately to 0.02 to 0.024 inches.

It has been found that by placing straight and offset sections of teeth on the same blade as described herein that a cut may be started with the straight section in the dental stone work and thereafer the offset saw teeth may be guided into the slot following the straight teeth whereby no chipping or altering of the cut occurs. It has been found that the life of such a saw blade is about doubled and that a straighter cut in the stone is provided apparently due to the increased cutting ability of the offset teeth which keeps the blade from dulling and also provides a faster cutting action.

The linear aligned teeth allow the blade to make the initial cut at the top of the dental arch at an area of close approximation of the teeth on the dental arch without damage to that area. Once past the dental teeth, the offset saw teeth may be safely used to rapidly finish the sawing and sectioning.

While a preferred embodiment of the invention has been described using specific terms, such description is for illustrative purposes only, and it is to be understood that changes and variations may be made without departing from the spirit or scope of the following claims.

What is claimed is:

1. A dental saw blade for sawing dental stone work comprising:
   a longitudinal shank portion extending the length of said blade;
   a first section having a number of saw teeth carried by said shank portion in generally linear alignment one behind the other;
   a second section of saw teeth carried by said shank portion in a laterally offset manner;
   said second section having a number of saw teeth in which next adjacent teeth are offset with respect to one another in opposite lateral directions relative to the linear alignment of said first section of saw teeth;
   said first and second sections joining one another enabling said second section of teeth to enter said cut following initiation by said first cut affording a faster and more accurate sawing of said stone work; and
   an intermediate section of teeth joining said first and second section wherein said teeth are offset gradually relative to said second section of teeth and blend said first and second sections of saw teeth;
   whereby said second section of teeth may be moved into a cut initiated by said first section of teeth with reduced likelihood of chipping or alteration of said dental stone material.

2. The structure of claim 1 wherein adjacent ones of said second number of saw teeth alternate in said opposite lateral offset directions.

3. The structure of claim 2 wherein said laterally offset saw teeth are inclined to one another.

* * * * *